(12) United States Patent
Rukhliada

(10) Patent No.: US 11,007,231 B1
(45) Date of Patent: May 18, 2021

(54) METHOD FOR SLOWING DOWN AGING IN WOMEN BY PROLONGING OVARIAN FUNCTION

(71) Applicant: Nikolai Rukhliada, St.Petersburg (RU)

(72) Inventor: Nikolai Rukhliada, St.Petersburg (RU)

( * ) Notice: Subject to any disclaimer, the term of this patent is extended or adjusted under 35 U.S.C. 154(b) by 0 days.

(21) Appl. No.: 16/947,991

(22) Filed: Aug. 27, 2020

(51) Int. Cl.
*A61K 35/54* (2015.01)
*C12N 5/071* (2010.01)
*A61K 9/00* (2006.01)

(52) U.S. Cl.
CPC ............ *A61K 35/54* (2013.01); *C12N 5/0682* (2013.01); *A61K 9/0019* (2013.01)

(58) Field of Classification Search
CPC ..... A61K 35/54; A61K 9/0019; C12N 5/0682
See application file for complete search history.

(56) References Cited

PUBLICATIONS

Mason et al., Transplantation of young ovaries to old mice increased life span in transplant recipients. The Journals of Gerontology, vol. 64A, No. 12 (Dec. 2009) pp. 1207-1211. (Year: 2009).*

Batchvarov et al., A grafted ovarian fragment recuse host fertility after chemotherapy. Molecular Human Reproduction, vol. 22, No. 12 (Dec. 1, 2016) pp. 1-10. (Year: 2016).*

Rukhliada, et al., Improvement of life expectancy in female mice by means of ovarian autologous step-by-step transplantation over therapy with estradiol. Global Reproduction, vol. 1 (2020) pp. 5-8. (Year: 2020).*

* cited by examiner

*Primary Examiner* — Kara D Johnson
(74) *Attorney, Agent, or Firm* — Dmitry S. Kryndushkin

(57) ABSTRACT

The main characteristic of method is that before the onset of menopause in women at age 30-45 years, part of the cortical and medulla layers of one or both ovaries is surgically resected and cryopreserved (frozen), and in perimenopause beginning, these tissues are autotransplanted subcutaneously in a form of suspension or small ovarian pieces prepared from thawed tissues fragments of their own ovaries. This "return" is repeatedly periodically each 4-6 months for 10-15 years. That helps to obtain normal level of ovarian antiage factors in blood till age 60-65 years, thus slowing aging.

4 Claims, No Drawings

METHOD FOR SLOWING DOWN AGING IN WOMEN BY PROLONGING OVARIAN FUNCTION

CROSS-REFERENCE TO RELATED APPLICATIONS

This application claims priority to provisional application 62/975,776 filed Feb. 13, 2020, the content of which is incorporated herein.

FIELD OF THE INVENTION

The invention relates to medicine, in particular, to gynecology, endocrinology, gerontology and can be used to increase the life expectancy of women.

BACKGROUND

There is a known way to prolong the life of women by prescribing estradiol drugs or metabolites as a component of menopausal hormone therapy [Gouw A M, Efe G, Barakat R, Preecha A, Roles of estrogen receptor-alpha in mediating life span: the hypothalamic deregulation hypothesis//Physiol Genomics. 2017 Feb. 1; 49(2):88-95; Taylor F I S, Tal A, Pal L, Li F, black DM//effects of oral vs transdermal estrogen therapy on sexual function in Early postmenopause: ancillary study Of the Kronos early estrogen prevention study (keeps)//JAMA Intern med. 2017 Oct. 1; 177(10): 1471-1479.].

The disadvantage of this method is that in this treatment option, the physiological effect results only from the estradiol component, and biologically active substances (and there are more than 100 of them) produced in the ovaries along with estradiol are not taken into account. Moreover, there are artificially synthesized no other antiage ovarian factors—so they are not available. This is why the anti-aging effectiveness of estrogen therapy is low. In addition, the appointment of estrogens containing drugs is strictly contraindicated in a number of conditions, and can also lead to the development of such dangerous complications as thrombosis.

The closest to the claimed method is to extend the life of mammals (mice) by allogenic transplantation of whole ovaries from young to old [Mason J. B., Cargill S. L., Anderson G B, Carey Jr.//Transplantation of young ovaries to old mice increased life span in transplant recipients//J Gerontol A Biol Sci Med Sci. 2009 December; 64(12):1207-11]. The disadvantage of the method chosen as a prototype is that due to the allogenic nature of the transplant, there are a number of problems associated with the graft rejection reaction. Moreover, the entire ovary is transplanted into the abdominal cavity, which eliminates the possibility for stage-by-stage restoration of ovarian function, and also requires laparotomy and general anestesia.

Also, with this method, it is impossible to periodically update the transplanted tissue, its dosage due to the absence of a conservation stage.

Cryopreservation and autotransplantation of ovarian tissue is used in oncofertility, showing possibility of autotransplants to produce estradiol after return [Salama M, Woodruff T K.//New advances in ovarian autotransplantation to restore fertility in cancer patients//Cancer Metastasis Rev. 2015 December; 34(4):807-82].

SUMMARY OF THE INVENTION

The purpose of the present invention is to provide the possibility of slowing down the aging of women by prolonging ovarian function without the use of allogenic ovarian tissues to prevent recipient graft reject phenomenon.

The result of the task to slow down aging in women is achieved by technology of ovarian tissue autologic transplantation, when before menopause the small portion of both cortical and medulla layers of ovaries resected, divided by pieces and cryopreserved (frozen); starting in perimenopause the tissues are thawed and reimplanted (autotransplanted) every 120-180 days subcutaneously in form of small pieces or cell suspension, along or without menopausal hormone therapy.

DETAILED DESCRIPTION OF THE INVENTION

In the claimed method, autotransplantation of ovarian tissue is performed. This eliminates the possibility of developing a "graft-recipient" rejection reaction, and also eliminates a number of ethical and legal issues related to allogeneic tissue and organ transplantation.

Obtaining and preserving autografts before menopause makes it possible to preserve ovarian tissue that is still actively functioning.

Harvesting and preservation of the complex of tissues of the cortical and medullary layers is due to the fact that it is the medullary layer that is responsible for inhibiting apoptosis and tissue survival during conservation. Cryopreservation of only the cortical layer, in contrast to the medullary-cortical layer complex, is characterized by worse graft survival.

Cryopreservation of ovarian tissue allows for reimplantation ("return") after an unlimited time, since the storage period of transplants in liquid nitrogen is calculated in tens of years. Between tissue collection and their return, the time period should be at least 3 years, since the return is carried out at the onset of menopause (1 year of absence of menstruation), and the sampling should be carried out before the hormonal markers of perimenopause described in the method (decrease in AMH, growth of FSH and LH) However, it is optimal to start step-by-step transplantation at the very beginning of menopause and with the beginning of menopausal hormone therapy.

For transplantation (return), after defrosting the fragment, it is mechanically crushed to form a coarse suspension, which is introduced subcutaneously through a thick needle. This method of transplantation eliminates the need for laparotomy or other intraabdominal intervention, is simple and does not require General anesthesia. The frequency of return of transplanted tissues is extremely important. It is known that ovarian tissue grafts after cryopreservation, defrosting and transplantation have a limited life span in the body. It is usually limited to 8-12 months. Therefore, the introduction of transplanted tissues at intervals of 120-180 days subcutaneously allows for continuous functioning of the graft for sufficient hormonal production. The combination of transplantation and menopausal hormone therapy is optimal, since the presence of functioning fragments of medullary substance increases the bioavailability of exogenous estradiol derivatives.

The combination of these differences makes it possible to achieve long-term ovarian function in menopausal women, and therefore increase life expectancy.

The method is performed as follows. In women before the transition to menopause at the age of 40-45 years, ovarian fragments are surgically obtained (approximately 5% of the volume) (for example, by laparoscopy). Excision of ovarian fragments should be accompanied by equal removal of the cortical and medullary layers. Preferably a wedge-shaped excision.

Criterion of adequacy of time for the undisturbed regular menstrual cycle, hormone AMH not below 1.2 ng/ml, FSH level lower 25 IU/L.

At the onset of the patient's perimenopause period, when it comes to the beginning of menopausal hormone therapy (usually more than 5 years after tissue sampling and preservation), along or without with the appointment of estradiol-containing drugs, the patient is periodically administered a fine-fragmented suspension prepared from defrosted ovarian fragments containing medullary and cortical substances. After defrosting at room temperature, when it reaches one or more capsules are opened, immediately under sterile conditions, the ovarian tissue is crushed mechanically until a fine-fragmented mass is obtained, which can be pushed through a syringe needle with a lumen diameter of about 2 mm. For a single injection, a volume of 1-2 cubic millimeters of tissue is sufficient. or tissue can be reimplanted via big gauge needle by pieces subcutaneously.

Example. Patient F. 45 L. went to the clinic of the Institute of emergency medicine in November 2013 for ovarian tissue preservation. She noted a regular menstrual cycle, anti-Muller hormone level of 1.4 ng/ml, FSH level of 18 IU/l. In accordance with the claimed method, laparoscopy, sampling of about 5% of the volume of each ovary (medullary and cortical tissue complex) and cryopreservation were performed. After 4 years, the woman noted the disappearance of menstruation, a change in the hormonal background AMG 0.4 ng/ml, FSH 65 IU/l. In November 2017 (4 years after sampling) menopausal hormone therapy was started, as well as the introduction of a suspension of defrosted ovarian tissues in accordance with the claimed method every 120-180 days subcutaneously. In the analysis-after six months, the normalization of FSH numbers to the level of premenopausal (up to 20 med/l). Observed for 3 years, with dermatological and endocrinological examination, there are no signs of aging associated with menopause (changes in the structure and density of the dermis, vascular disorders, menopausal syndrome).

The claimed method is as close as possible to the physiological one. The absence of the need to use allotments immediately eliminates a large number of complications associated with the development of the transplant rejection reaction (inefficiency, inflammation, suppuration), as well as the need for immunosuppressive therapy after tissue return. The absence of the need to transplant "foreign tissues" also eliminates ethical aspects and legal issues, since this technology does not fall under the legal provisions of the law on tissue transplantation. With this method, there is no need for HLA tissue typing and donor selection. The use of autotissues and their preservation in the period of life when their partial withdrawal does not lead to the development of physiological changes, and the return to the body in menopause, when the introduction of these substances is extremely important for slowing down aging is the main advantage of the invention.

Examples of Use of the Invention

1. In women, before entering menopause at the age of 30-45, ovarian fragments are surgically obtained by laparoscopy e.g. Excision of ovarian fragments should be accompanied by equal removal of the cortical and medulla layers. Preferably a wedge-shaped excision for fragments obtaining. That doesn't effect significantly on the ovarian reserve. The total volume of resection is no more than 200 cubic mm (less than 5% of total ovarian volume). Obtaining and preserving autografts before menopause makes it possible to preserve ovarian tissue that is still actively functioning.

2. Criterion of adequacy of time for the fragments obtaining are undisturbed regular menstrual cycle, anti mullerian hormone blood level above 1.0 ng/ml, follicle stimulating hormone level below 25 IU/L.

3. Immediately after resection ovarian fragments are divided into particles no more than 2×1×1 mm in sterile conditions—to form 30-40 autotransplants and cryopreserved by known methods each in separate container to be thawed further separately. Tissue is stored in liquid nitrogen for an unlimited time.

4. When a patient enters perimenopause, when it is the beginning of MHT, along (or without) with the appointment of estradiol-containing drugs, the patient is periodically injected subcutaneously with autotransplants (whole or fragmented suspension) prepared from thawed ovarian fragments containing medullary and cortical substances of own ovaries. Such injections are recommended once every 120-180 days along with MHT. Thus the technique helps to restore ovarian anti-age factors by means of medulla-cortex autotransplantation.

5. After defrosting by known methods, the ovarian fragments are either autotransplanted as a whole (2×1×1 mm fragment), or cut mechanically until a fragmented mass is obtained, which can be pushed through a syringe needle with a lumen diameter of about 2 mm. For a single injection, a volume of 2 cubic millimeters of tissue is sufficient. The mass is mixed in a syringe with a small (1-2 ml) amount of saline solution and injected subcutaneously through a needle with a thick lumen—the procedure of autotransplantation.

I claim:

1. A method for slowing the aging of women, comprising:
    (a) harvesting ovarian tissue from a human subject before menopause, characterized in that at least part of the cortical and medullary layers of an ovary is harvested to produce the ovarian tissue;
    (b) preparing a particulate ovarian tissue;
    (c) cryopreserving the particulate ovarian tissue to produce a cryopreserved particulate ovarian tissue;
    (d) thawing at least a portion of the cryopreserved particulate ovarian tissue at the onset of menopause to produce a thawed particulate ovarian tissue;
    (e) suspending the thawed particulate ovarian tissue in a saline solution to produce a suspended ovarian tissue;
    (f) injecting the suspended ovarian tissue subcutaneously into the subject; and
    (g) repeating steps (d)-(f) once every 120-180 days.

2. The method of claim 1, wherein the thawed particulate ovarian tissue is further fragmented before injecting the suspended ovarian tissue subcutaneously into the subject.

3. The method of claim 2, wherein the thawed particulate ovarian tissue is fragmented by a mechanical cut.

4. A method for slowing the aging of women, comprising:
    (a) harvesting ovarian tissue from a human subject before menopause, characterized in that at least part of the cortical and medullary layers of an ovary is harvested to produce the ovarian tissue;
    (b) preparing a particulate ovarian tissue;
    (c) cryopreserving the particulate ovarian tissue to produce a cryopreserved particulate ovarian tissue;
    (d) thawing at least a portion of the cryopreserved particulate ovarian tissue at the onset of menopause to produce a thawed particulate ovarian tissue;

(e) without further fragmenting, injecting the thawed particulate ovarian tissue subcutaneously into the subject; and
(f) repeating steps (d)-(e) once every 120-180 days.

* * * * *